(12) United States Patent
Egana-Erazo et al.

(10) Patent No.: US 11,666,616 B2
(45) Date of Patent: Jun. 6, 2023

(54) USE OF PHOTOSYNTHETIC SCAFFOLDS IN TISSUE ENGINEERING

(71) Applicant: SYMBIOX, INC., San Diego, CA (US)

(72) Inventors: Jose-Tomas Egana-Erazo, Munich (DE); Hans-Gunther Machens, Munich (DE); Ursula Hopfner, Munich (DE); Joerg Nickelsen, Munich (DE)

(73) Assignee: SYMBIOX, INC., San Diego, CA (US)

( * ) Notice: Subject to any disclaimer, the term of this patent is extended or adjusted under 35 U.S.C. 154(b) by 437 days.

(21) Appl. No.: 17/021,621

(22) Filed: Sep. 15, 2020

(65) Prior Publication Data

US 2020/0405796 A1 Dec. 31, 2020

Related U.S. Application Data

(60) Continuation of application No. 15/845,016, filed on Dec. 18, 2017, now Pat. No. 11,207,362, which is a division of application No. 14/869,930, filed on Sep. 29, 2015, now Pat. No. 9,849,150, which is a continuation of application No. 13/636,402, filed as application No. PCT/EP2011/001423 on Mar. 22, 2011, now Pat. No. 9,144,589.

(30) Foreign Application Priority Data

Mar. 22, 2010 (EP) .................................. 10003008

(51) Int. Cl.
| | | |
|---|---|---|
| *A61K 36/05* | (2006.01) | |
| *A61L 24/00* | (2006.01) | |
| *A61L 27/38* | (2006.01) | |
| *A61L 27/60* | (2006.01) | |
| *C12N 5/00* | (2006.01) | |
| *C12N 1/12* | (2006.01) | |
| *A61L 27/50* | (2006.01) | |
| *A61L 24/10* | (2006.01) | |
| *A61L 26/00* | (2006.01) | |
| *A61L 27/24* | (2006.01) | |

(52) U.S. Cl.
CPC .......... *A61K 36/05* (2013.01); *A61L 24/0005* (2013.01); *A61L 24/102* (2013.01); *A61L 24/106* (2013.01); *A61L 26/0033* (2013.01); *A61L 26/0042* (2013.01); *A61L 26/0057* (2013.01); *A61L 27/24* (2013.01); *A61L 27/3804* (2013.01); *A61L 27/50* (2013.01); *A61L 27/60* (2013.01); *C12N 1/12* (2013.01); *C12N 5/0068* (2013.01); *A61L 2430/34* (2013.01); *C12N 2502/70* (2013.01); *C12N 2533/54* (2013.01)

(58) Field of Classification Search
None
See application file for complete search history.

(56) References Cited

U.S. PATENT DOCUMENTS

| | | |
|---|---|---|
| 2004/0133188 A1 | 7/2004 | Vardi et al. |
| 2005/0136092 A1 | 6/2005 | Rotem et al. |

FOREIGN PATENT DOCUMENTS

| | | |
|---|---|---|
| EP | 1351623 A1 | 10/2003 |
| WO | 2008062417 A2 | 5/2008 |
| WO | 2008065660 A2 | 6/2008 |

OTHER PUBLICATIONS

Rasala et al., "The microalga *Chlamydomonas reinhardtii* as a platform for the production of human protein thereapeutics." Biogengineered Bugs 2.1 (2011): 50-54. (Year: 2011).
Ahmed et al. "Fibrin: A versatile scaffold for tissue engineering applications" Tissue Engineering 14(2): 199-215, 2008.
Bloch et al., "Photosynthetic oxygen generator for bioartificial pancrease," Tissue Engineering 12(2): 337-344. 2006.
International Search Report dated Apr. 28, 2011 in PCT/EP2011/001423 filed Mar. 22, 2011.
Zhu et al. "Design properties of hydrogel tissue-engineering scaffolds", Expert Review of Medical Devices 8: 607-626, 2011.

*Primary Examiner* — Emily A Cordas
(74) *Attorney, Agent, or Firm* — Procopio, Cory, Hargreaves & Savitch LLP

(57) ABSTRACT

The present invention is concerned with a photosynthetic scaffold that delivers oxygen and its uses for tissue engineering and the treatment of ischemia.

16 Claims, 7 Drawing Sheets

USE OF PHOTOSYNTHETIC SCAFFOLDS IN TISSUE ENGINEERING

CROSS-REFERENCE TO RELATED APPLICATIONS

Figure 1:
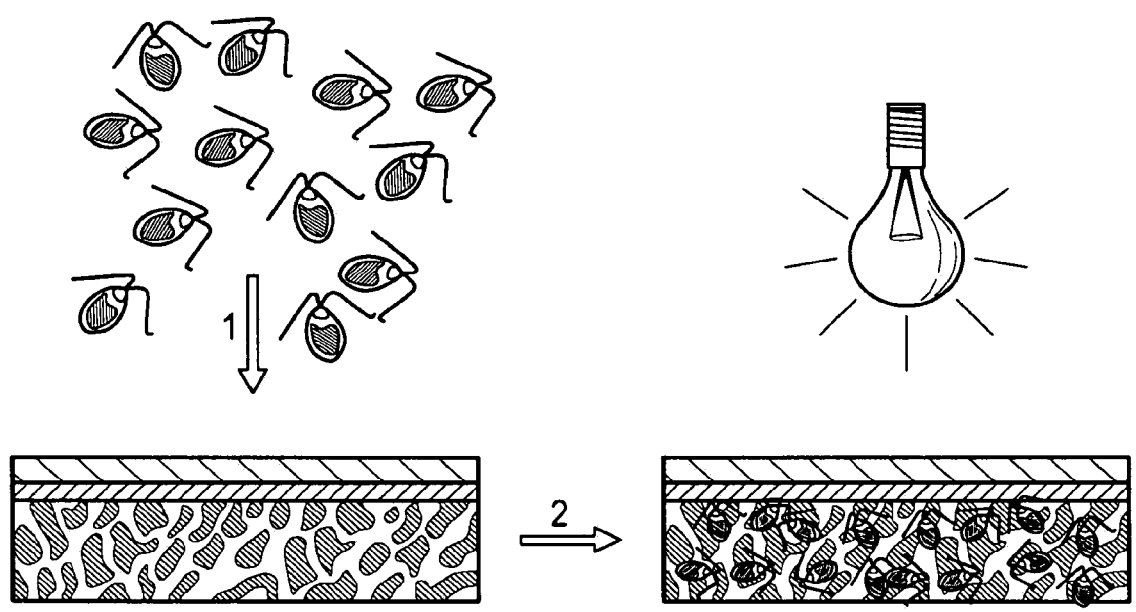

This application is a continuation of U.S. patent application Ser. No. 15/845,016, filed on Dec. 18, 2017, which is a divisional of U.S. patent application Ser. No. 14/869,930, filed on Sep. 29, 2015, now U.S. Pat. No. 9,849,150, which is a continuation of U.S. patent application Ser. No. 13/636,402, filed on Dec. 20, 2012, now U.S. Pat. No. 9,144,589, which is the national stage of application no. PCT/EP2011/001423 on Mar. 22, 2011, all of which are hereby incorporated by reference in their entirety.

The present invention is concerned with a photosynthetic scaffold that delivers oxygen and its uses for tissue engineering and the treatment of ischemia.

It is known to use tissue engineering for growing tissue and scaffolds to be used for this purpose are also known. Tissue engineering can be described as: "An interdisciplinary field that applies the principles of engineering and life science on the development of biological substitutes that restore, maintain or improve tissue function" (Vacanti J P, Science 1993). Although this approach is promising, several problems are associated with tissue engineering.

Due to lack of vascularisation, one of the major problems in tissue engineering, repair and regeneration of tissue is the delivery of oxygen and nutrients. New technologies to restore, maintain and improve tissue function, and also to build new tissues, like skin, are currently in development. Under culture conditions and for monolayers oxygen and nutrients can be supplied by external ways. However, similar approaches are difficult to apply for growing three-dimensional multilayer tissues in vitro or in vivo. Lack of oxygen is in particular a problem for growing tissue in vivo and fully satisfying technical solutions to supply oxygen to growing tissue are still missing. During the process of tissue regeneration, oxygen and nutrients can be delivered only after a functional vascular network has been created. However, vascularisation is a slow process and angiogenic failure or dysfunction results in the loss or degradation of the engrafted tissue. In an approach to provide for faster vascularisation of tissue constructs, thereby avoiding hypoxia, some methods have been developed, which are still not satisfying.

Thus, in one approach, microspheres were used for providing different growth factors to enhance development and maturation of blood vessels. Further approaches include the use of bioreactors, scaffolds with artificial microvasculature, oxygen carriers and hyperbaric oxygen chambers (see Review by Maida J., Klein T. J., Upton Z. The roles of hypoxia and the in vitro engineering of tissues. Tissue Eng. 13, 2153, 2007). Maida et al., report about enhancements in angiogenesis or vasculogenesis after in vivo implantation of scaffolds by the incorporation of endothelial cells, genetically modified cells or recombinant growth factors. Although all these technologies help in shortening the time required for regenerating vascular networks, the problem of lacking oxygen at the time of in vivo implantation remains unsolved.

The lack of vascularisation at the time of in vivo implantation is critical for the cell survival and tissue regeneration. It has already been suggested that hypoxia could be partially resolved by the use of oxygen carriers. For example T. Henkel-Honke et al. (Reviewed by Henkel-Honke T., Oleg M. Artificial oxygen carriers: A current review. AANA J. 75, 205-211, 2007) mention the incorporation of oxygen carriers like hemoglobin or perfluorocarbons in scaffolds for tissue engineering. Although these carriers are able to provide oxygen immediately, they do not provide a constant source of oxygen and, thus, are useful only for a short period of time.

Moreover, in EP 1 351 623 implantable devices containing living cells in a chamber are disclosed for the release of substances out of the chamber. The purpose of such device is to carry and maintain functional cells, wherein the functional cells are cells that express and secrete a substance that is necessary for an organism in which the device has been implanted. The functional cells shall produce substances such as insulin or testosterone which are secreted into the organism. In order to maintain the functional cells in the device, photosynthetic cells are provided in a second chamber, separated by a semi-permeable wall that delivers oxygen to the functional cells. To maintain the photosynthetic cells that can grow only in the presence of light the cells are illuminated by a light source in the chamber. Thus, the oxygen level within the chamber can be maintained on a predetermined level.

Scaffolds for use in tissue engineering are known for growing tissue in vitro as well as in vivo, and are extensively described in the literature. Scaffolds provide a three-dimensional framework for cells to attach and proliferate. They can be used in vitro to grow cells and build artificial tissues, they can also be used for regeneration and repair of tissue on site. When used in vivo, cells will grow and populate the scaffolds. In this approach the scaffolds are used only as structural matrix to facilitate tissue growth and regeneration in vivo. This type of scaffold is known for regeneration of tissue, like skin, bone, cartilage and nerve and is commercially available. Particularly for chronic and massive skin wounds scaffolds are widely used. However, the problem of oxygen delivery to the growing cells has not been solved until now.

However, for growing tissue, i.e. when growing cells are forming tissue architecture in complex structures instead of a monolayer of cells, supply of oxygen becomes a problem that has not been solved until now. Thus, it is an object of the present invention to provide a continuous supply of oxygen for growing tissues, in vivo and ex vivo, in particular to provide oxygen until vascularisation allows the survival of the tissue. Moreover, it is an object of the present invention to provide oxygen supply which is not harmful to the cells and does neither interfere with the growth nor produce substances that are harmful to the organism. A further object of the present invention is to provide a carrier for tissue that can deliver oxygen constantly, thereby decreasing hypoxia and improving tissue survival and regeneration. Furthermore, it was an object of the present invention to provide an oxygen source that can be regulated according to the needs of the tissue.

The above mentioned objects are solved by providing a photosynthetic scaffold as defined in claim 1. According to the present invention a scaffold is provided which is suitable for use in in vitro and in vivo tissue engineering. The scaffold comprises photosynthetic cells embedded in its structure and thereby delivers oxygen and nutrients to growing cells. It is particularly surprising that it is possible to allow survival of autologous cells that are built by the organism for repair or regeneration by providing the scaffold of the present invention.

In particular, this scaffold can be used to enhance the regeneration of damaged, injured or missing tissue. The scaffold of the present invention comprises photosynthetic cells which can deliver oxygen into the surrounding and, thus, hinder hypoxia and increase tissue regeneration independently of blood perfusion or vascularisation. In other words, the photosynthetic scaffold of the present invention allows to grow multilayered tissue which can survive without vascularisation or the supply by blood vessels for a longer time. The present invention surprisingly provides a tool for delivering oxygen to growing cells in a sufficient and appropriate way and, thus, can be used for the treatment of several pathological conditions including tissue ischemia and can be used for regeneration and repair of tissue.

The problem as outlined above can be solved by providing a photosynthetic scaffold as defined in the claims.

The term "scaffold" when used in the present application refers to a structure or carrier matrix to which cells can attach or on which cells can proliferate.

The term "photosynthetic cells" as used in the present application shall comprise cells and cell organisms that are photosynthetically active, i.e. photosynthetic cells as well as isolated chloroplasts as long as they release oxygen.

The term "tissue" as used in the present application shall refer to any type of tissue in a mammalian organism, and particularly to dermal, bone, nerve, cartilage and blood tissue.

Surprisingly it was found that photosynthetic cells can be incorporated in known scaffolds for tissue engineering where they remain active and can deliver oxygen constantly. Moreover, it was found that photosynthetic cells are compatible with the growth of mammalian cells such as fibroblasts, enhancing their viability and proliferation under hypoxic conditions. Although both types of cells have different requirements regarding nutrients, they can grow together on a carrier that provides the necessary nutrients.

The photosynthetic cells used for the scaffold of the present invention can be any type of cells that are able to grow and to be photosynthetically active. The photosynthetic cells used according to the present invention are those that are active in the presence of cells derived from different tissues, like dermal, bone and nerve tissue as well as blood tissue. In a preferred embodiment the photosynthetic cells used for the scaffold of the present invention are unicellular algae from the genus *Chlamydomonas*, in particular *Chlamydomonas reinhardtii* which can grow and maintain photosynthesis thereby delivering oxygen. Thus, by incorporating the photosynthetic cells in a scaffold, a "photosynthetic scaffold" is obtained, which can continuously release oxygen, providing the basis for tissue growth and regeneration.

The conditions and nutrients necessary for growth of mammalian and photosynthetic cells in the scaffold are known to the skilled person and optimal conditions can be obtained by routine experiments. Methods that are useful in this regard can be found for example in M. Butler; Animal Cell Culture and Technology; 2nd ed. BIOS Scientific, 2004. These known technologies together with the photosynthetic scaffold of the present invention can be used to develop complex multi-cellular and multilayered structures in vitro as well as in vivo. Thus, with the present invention it is possible to co-culture several cell types in different biomaterials. To allow the photosynthetic cells to grow on the scaffold, the scaffold preferably is provided with nutrients that are necessary for these cells which are known to the skilled person. The nutrients can be incorporated in the scaffold or can be part of the scaffold as is known to the skilled person. In one embodiment nutrients can be incorporated in a porous structure of the scaffold and are delivered with time. Furthermore, a medium for maintaining the photosynthetic scaffold can be applied in predetermined time periods; any medium known for maintaining photosynthetic cells like algae can be used. The culture of photosynthetic cells, particularly algae, more particularly cells of *Chlamydomonas* is well known in the art.

To optimize the conditions for growing both the engineered tissue and the photosynthetic cells, routine experiments can be made by the skilled person. The conditions are found by growing the cells together and monitoring the growth. To test the viability of both types of cells, i.e. photosynthetic cells and mammalian tissue cells, tests can be used that are known to the skilled person. In a preferred embodiment RNA is determined in the cells and is compared to the amount of RNA of average healthy cells. If the percentage of RNA of cells from the tissue grown on the tissue scaffold is in a range of 80 to 120% of the RNA content of a "normal" cell, i.e. an average healthy cell of the same type, the viability is sufficient. If the percentage is below 50% the tissue and/or the algae cells are in a bad condition and nutrients and environment should be adapted accordingly.

It has been found that isolated chloroplasts, sometimes even after freezing, can maintain their photosynthetic activity at least for some hours or even days or weeks. In a further embodiment of the present invention, photosynthetic cells can be fully or partially replaced by isolated chloroplasts, which can also release oxygen.

The scaffold of the present invention can comprise the photosynthetic cells and/or chloroplasts in their natural form. It is also possible, particularly to avoid immunological reactions, to protect the cells or isolated chloroplasts by encapsulation with a permeable immunologically inert material. Such materials and methods for encapsulation are well known in the art and the known methods and materials can be used for the present invention. Examples for a permeable immunologically inert material are natural or synthetic polymers that are physiologically acceptable, i.e. do not interfere with the growth of the tissue and do not disturb the viability of the cells and/or chloroplasts. Examples are hydrogels or alginate. Moreover, it is possible by encapsulation to modify the activity of the photosynthetic cells and/or chloroplasts in the scaffold. For example, by regulating the biodegradability or transparency it is possible to enhance or decrease the activity of the cells and/or chloroplasts and, thereby, to regulate the level of oxygen production.

Moreover, in a further embodiment of the present invention, the cells and/or chloroplasts used for the photosynthetic scaffold of the present invention can be modified regarding their nutrient requirements or light requirements. Thereby, the scaffold can be adapted to the light available and thereby, oxygen release can also be adapted accordingly.

Photosynthetic cells and/or isolated chloroplasts that have been adapted as to the light requirements are known in the art. Thus, it is possible in specific cases to adapt algae cells and/or chloroplasts for their light requirements depending on the light available and by adding these adapted cells or chloroplasts the activity and, thereby, the oxygen release can be adapted accordingly.

The scaffold that supports the photosynthetic cells as well as the growing tissue can be any scaffold that is known for use for tissue engineering. Material for producing such scaffolds is well known in the art and it is commonly a biocompatible polymer which can be synthetic or natural or a combination of both. Biocompatible in this regards means any material that is compatible with living cells, tissues, organs, or systems, and poses no risk of injury or toxicity, and is not or hardly rejected by the immune system. In a preferred embodiment, biodegradability, nature and structure of the scaffold can be adapted by methods well known to the skilled artisan. Commonly used materials are natural materials like alginate, chitosan, agarose, gelatine, collagen or .kappa.-carragenan, or synthetic products like polylysin, polyvinylalcohol, polyethylene glycol or derivatives thereof or mixtures of these products. Collagen and collageneous material or hyaluronic acid as well as derivatives thereof are particularly useful. Furthermore, hydrogels or webs made from fibers or spider silk can also be used. The material used for the scaffold can be biodegradable, i.e. it is degraded with time. In a preferred embodiment the material has a predetermined biodegradability, i.e. it degrades after and/or within a predetermined time period. In another embodiment polymers can be used for preparing the scaffold, that are inert, i.e. do not react with tissue, photosynthetic cells, body fluids, skin or any drug that might be present, and can be deleted when no longer needed. Moreover, decellularized tissues or organs can also be used as scaffolds. The material and its structure are uncritical as long as photosynthetic cells or isolated chloroplasts can be attached, can proliferate and are able to release oxygen to the surroundings.

The scaffold serving as carrier for the cells can have any form that is useful for supporting cells or tissue respectively. Any form known for tissue engineering is suitable, for example it can be a porous substrate, a network, or a woven or non-woven fabric. Any form is useful as long as both types of cells can grow and receive nutrients and oxygen.

The pore size or mesh size of the scaffold is a property that can have an influence on cell attachment, growth and ingrowth of blood vessels. Research on tissue engineering has shown the optimal properties for such carriers and these are known to the skilled person. Thus, the skilled person can choose the best suited pore size or mesh size based on his knowledge and/or with a few routine tests that are described in the prior art.

In one embodiment of the present invention the carrier is a three-dimensional scaffold as described above.

In another embodiment of the present invention the carrier is built on-site from a fibrin solution which can be applied at the site where the photosynthetic cells shall grow, for example a wound. In this embodiment a fibrin solution is used which is applied and builds a fibrinogen network. The advantage is that on the one hand the photosynthetic cells can be applied, for example by spraying, at the site where the photosynthetic scaffold is necessary. On the other hand the fibrinogen is gradually destroyed in the body but allows the cells to build a network. As fibrin has adhesive properties a fibrin solution comprising photosynthetic cells can adhere to the tissue where it has been applied and adheres at the surface and creates a network that immobilizes the photosynthetic cells on the surface of the skin or another site in the body. The photosynthetic cells can then grow and at the same time deliver oxygen to their environment and, thereby, can supply oxygen to the defect tissue of the skin or organ they are growing on. The fibrin network is support and nutrient at the same time. A fibrin solution comprising photosynthetic cells can also be used to apply a further layer of cells to an already growing tissue if further oxygen supplying cells are necessary.

In another embodiment the photosynthetic scaffold is in the form of a wound dressing or a surgical suture. The carrier for the wound dressing is made from a biocompatible material, that preferably is permeable or semi-permeable. In a preferred embodiment the support layer of the wound dressing is a membrane that is semi-permeable for oxygen. An example for such material is silicone. In another embodiment the support layer is made from a membrane that is permeable for gas to allow gas exchange. The photosynthetic cells in this embodiment are attached to the support layer and, thus, can easily be removed when they are no longer necessary for providing oxygen.

The photosynthetic scaffold of the present invention is used to grow and support tissue, preferably tissue like skin, nerve, bone, cartilage, and blood tissue, particularly dermal tissue, nerve tissue or bone tissue, in other words tissue to regenerate or to repair damaged or injured parts of the body. The photosynthetic scaffold of the present invention can be directly applied to an injured site and allows growing of tissue on-site and thereby supports and particularly provides oxygen for the growing cells.

The photosynthetic scaffolds of the present invention as claimed and described in this specification and all the embodiments thereof, as claimed and described, can be used for treatment of wounds or injuries, particularly for the treatment of damaged or injured tissue like skin, nerve, bone, cartilage, and blood tissue, particularly dermal tissue, nerve tissue or bone tissue.

In one embodiment the tissue scaffold of the present invention is used to let grow (autologous) fibroblasts in bigger wounds. Fibroblasts can be grown together with the photosynthetic cells of the present invention because the photosynthetic cells are compatible with mammalian cells, i.e. do not excrete any substance that is detrimental to the mammalian cells or organisms. On the other hand, the photosynthetic cells, like *Chlamydomonas* cells can grow in the presence of fibroblasts and can provide oxygen to them. By using the scaffold of the present invention the tissue can grow to cover big wounds. The growth can continue and the new tissue can cover the wound even without angiogenesis because of the oxygen supply by the photosynthetic cells.

If the photosynthetic scaffold of the present invention is used on-site, it has to be provided with nutrients for growing the algae cells but not necessarily with nutrients for the tissue to be grown, if these are delivered by the body.

Co-culture systems might be useful for developing tissue constructs on a higher level of cellular organization. Thus, in one embodiment of the present invention the scaffold is used for co-culture systems for in vitro tissue engineering.

Furthermore it is possible to provide the photosynthetic scaffold of the present invention with nutrients that are included in the pores or meshes of the scaffold material and are released with time. It is also possible, to include into the scaffold microencapsulated nutrients having a controlled release pattern. Thereby, the nutrient need of the growing cells as well as of the photosynthetic cells can be satisfied.

It can be advantageous to use material whose degradability is adaptable such that the scaffold is present as long as it is needed and is degraded when no longer necessary. For this purpose a material should be degradable to products that are not harmful for the organism. Those materials are known in the art for producing scaffolds and the known materials can be used for the scaffolds of the present invention.

In a preferred embodiment the scaffold is made from a biocompatible and biodegradable material, in particular a material with adapted biodegradability. Methods for adapting or influencing the biodegradability are well known to the skilled person.

In one embodiment of the present invention the scaffolds are used for the growth of autologous tissue in vivo. In another embodiment the scaffolds can also be used for growing tissue in vitro and, optionally transplanting the grown tissue to a site where the tissue is required. Thus, the photosynthetic scaffold of the present invention can be used to engineer tissue, like dermal, nerve or bone tissue in vitro and to apply the scaffold with the grown tissue to a site where tissue is damaged, injured or missing, for example a massive wound. By using the scaffold of the present invention the photosynthetic cells provide oxygen to the growing cells and hinder ischemia or damage by missing oxygen.

In a further embodiment the photosynthetic scaffold of the present invention can also be used for the local delivery of oxygen to tissue during tissue ischemia, such as organs that are not or not sufficiently provided with oxygen, for example heart tissue after a heart infarction. In a preferred embodiment of this aspect of the present invention the scaffold can be built on site, for example by applying a fibrin glue solution over the tissue which then forms a network in situ. As fibrin has adhesive properties, such network immobilizes the photosynthetic cells on the surface of the tissue where it has been supplied. In this embodiment the scaffold is a photosynthetic biofilm which increases the local oxygen concentration. Such photosynthetic bio-film can be used in a therapeutic approach for the treatment of ischemic tissue.

In another approach, the photosynthetic scaffold of the present invention is provided in a small form such that it can be circulated. In this approach small circulating photosynthetic scaffolds can be used to deliver oxygen systemically, thus increasing the concentration of oxygen in blood. This approach could be used to treat hemorrhage or anemia, representing several advantages compared to current technologies, which are based on oxygen carriers or blood transplantation procedures. For this approach scaffolds can be used with photosynthetic cells and/or chloroplasts which are preferably encapsulated by a oxygen permeable capsule to protect the photosynthetic cells and/or chloroplasts from immunological reactions.

The photosynthetic cells used according to the present invention are preferably cells from the genus *Chlamydomonas* which can grow and maintain photosynthetic activity thereby delivering oxygen after seeding in the scaffolds. *Chlamydomonas* are unicellular green algae with a prominent chloroplast and cilia that lives normally in soil, lakes and streams. *Chlamydomonas* is particularly useful as photosynthetic organism because it is generally regarded as safe (GRAS) with no known viral or bacterial pathogen and is deemed to lack bacterial endotoxin contamination. Moreover, it is a well known organism which has been widely used for genetic studies and much is known about its biology, including the entire genome. Furthermore, *Chlamydomonas* can be used under GMP conditions. As soon as it is no longer needed it can be easily eliminated from the host by light deprivation. *Chlamydomonas* can be transformed by known methods and, thus, can be modified to provide useful properties including the secretion of functional recombinant human proteins.

Methods for genetically engineering photosynthetic cells, like *Chlamydomonas*, are well known in the art, see for example Leon-Banares et al., Transgenic microalgae as green cell-factories. Trends Biotechnol. 2004; 22: 45. Therefore, in one embodiment the scaffold of the present invention comprises photosynthetic cells that have been genetically engineered to contain nucleic acids encoding for at least one bioactive molecule, such as cytokines, growth factors or angiogenesis factors, or drugs for treating inflammation and/or infections, for example at least one pro-angiogenic growth factor, such as VEGF and bFGF and/or at least one antibacterial or antiviral drug and/or at least one anti-inflammatory agent. This type of scaffold is particularly suited for use for treatment or prevention of inflammation and/or for treatment of injuries and damages, particularly injuries and damages of tissue like skin, nerve, bone, cartilage, and blood tissue, particularly dermal tissue, nerve tissue or bone tissue. In one embodiment this type of scaffold is for use for treatment of non-healing wounds and/or chronic wounds and/or massive wounds.

The scaffold can comprise only genetically engineered photosynthetic cells or a combination of wild-type photosynthetic cells and genetically engineered cells. By using genetically engineered cells, the photosynthetic scaffold of the present invention can provide oxygen and other bioactive molecules which can be secreted continuously or on demand. With this approach, key processes for tissue survival and regeneration can be modulated. Methods for modulating expression of molecules are well known to the skilled person. Expression can be controlled by inducible or conditional promoters. Thus, release of recombinant molecules can be adapted to the need of a patient and by local and/or continued release of molecules like growth factors or pro-angiogenic factors the survival of growing cells and multilayered tissue can be improved. In another embodiment molecules for treating inflammation, scarring and/or infections at the wound area are released intermittently or continuously to improve the healing process. Thus, the photosynthetic scaffold of the present invention can comprise a combination of wild-type cells, genetically modified photosynthetic cells that produce recombinant growth factors and/or genetically modified photosynthetic cells that produce therapeutical agents like anti-inflammatory agents or anti-bacterial agents. Thus, the scaffold of the present invention that provides oxygen and biologically active molecules is particularly valuable for the treatment of non healing wounds which are commonly infected and non vascularized.

As outlined above, the photosynthetic scaffold of the present invention can be used for tissue engineering in vivo and in vitro. It was found that in vitro photosynthetic cells, particularly *Chlamydomonas* cells can be cultured in a scaffold and thereby provide oxygen in a light dependent manner. In particular it was found that *Chlamydomonas* can be co-cultured with tissue cells like fibroblasts. Both are compatible with each other. The oxygen provided by the photosynthetic cells fulfills the metabolic requirements of fibroblasts under hypoxic conditions, enhancing survival and proliferation. Thus, with the new scaffold of the present invention tissue cells, particularly fibroblasts can be grown in a blood independent way which is of particular interest in the absence of appropriate vascularization.

On the other hand it was found that photosynthetic cells, particularly *Chlamydomonas* can be co-cultured with fibroblasts growing in a wound and can deliver oxygen to the fibroblasts in a blood independent way which is particularly useful for patients with chronic wounds where vascularization can also be a problem. Therefore, the photosynthetic scaffold of the present invention is particularly useful for treatment of wounds in diabetic patients, elder patients or for treatment of massive wounds like burns.

For the above embodiments a scaffold built from collagenous material has been found particularly useful.

Moreover, it has been found that instead of or additional to using complete photosynthetic cells it is also possible to use the photosynthetically active organisms thereof, i.e. chloroplasts, and protoplasts from *Vaucheria litorea* are particularly preferred. It has been found that these protoplasts even in isolated form are able to survive for some time, i.e. up to some months, and to maintain their activity, i.e. they can deliver oxygen continuously outside the cell (Rumpho M E, Summer E J, Manhart J R. Solar-powered sea slugs. Mollusc/algal chloroplast symbiosis. Plant Physiol.

2000; 123: 29). Therefore, in one embodiment of the present invention these chloroplasts are used in the photosynthetic scaffold instead of or in addition to photosynthetic cells from *Chlamydomonas*. A combination can be useful if for example different light sensitivity is used to have maximum activity over the day.

According to the present invention either one type of photosynthetic cells or more types of photosynthetic cells optionally together with chloroplasts can be used in the scaffold for providing oxygen. By using a combination optimal conditions can be created particularly if cells having different light sensitivity are used. In this way a maximum activity can be obtained all the time.

The present invention provides a carrier for growing cells that is able to deliver oxygen continuously and in-situ. The invention allows the application of oxygen producing cells wherever they are needed in the organism. Thus, a valuable tool to promote regeneration and to treat hypoxia is presented here.

The photosynthetic scaffold of the present invention can provide oxygen to growing cells. Therefore, another aspect of the present invention is the use of at least one type of photosynthetically active cells for providing oxygen to growing, damaged or injured cells or tissue in a mammalian organism in need of oxygen. In a preferred embodiment the photosynthetically active cells are used for providing oxygen to regenerating skin or regenerating bone, particularly when the subject or organism is a mammal, preferably a human being or a rodent.

As the scaffold of the present invention can be used for providing oxygen to growing cells in vivo as well as in vitro the scaffold can be used in a method wherein first cells are grown in vitro on the scaffold of the present invention and, as the scaffold is biocompatible, the scaffold is then inserted on the site where the cells are needed and can further grow on that place. In this embodiment it is particularly useful if the scaffold is made of a material that is degraded with time. Therefore, another aspect of the present invention is a photosynthetically active scaffold of the present invention for use for growing tissue in vitro and inserting the scaffold with the growing cells on the site where the cells are needed.

This embodiment is particularly useful for preparing skin grafts or bone grafts, particularly for the repair of damaged, injured or missing skin.

A further aspect of the present invention is the use of photosynthetic cells for preparing a composition for use for treatment of hypoxia.

The photosynthetic scaffold of the present invention is particularly useful for engineering dermal tissue which is grown on the scaffold on-site. In a preferred embodiment the photosynthetic scaffold of the present is used for regeneration or repair of damaged, injured or missing skin, particularly for great wounds like burns or ulceration. The photosynthetic cells can grow easily on the surface in the presence of light. When the photosynthetic cells are no longer necessary, one can get rid of the cells by separating them from light or by using a herbicide.

Furthermore it has been found that the regeneration or repair of damaged or missing tissue can be further improved by accelerating or improving vascularisation. It has been found that the photosynthetic cells of *Chlamydomonas* can be genetically engineered to express foreign proteins that are valuable for the growth and maintenance of the cell tissue, for example growth factors or pro-angiogenic factors. *Chlamydomonas* is a genus that is well known to integrate DNA into the genome to express foreign genes. Therefore, in a preferred embodiment at least part of the algae cells incorporated in the photosynthetic scaffold of the present invention are genetically engineered *Chlamydomonas* cells comprising DNA encoding proteins or polypeptides that are useful for growing or maintaining tissue culture or natural tissue.

In one embodiment *Chlamydomonas* cells are used which have been genetically engineered to comprise a nucleic acid encoding at least one growth factor and/or pro-angiogenic factor. By using this genetically engineered *Chlamydomonas* cell for growing tissue not only oxygen is provided for enhanced viability but at the same time factors are excreted which provide for creation of vessels and, thus, for improved growth and maintenance of the tissue.

Therefore, in one embodiment part of the photosynthetic cells are genetically engineered cells which express one or more pro-angiogenic factors. Particularly preferred is the use of the pro-angiogenic factors VEGF or FGF. A further advantage by using some genetically engineered photosynthetic cells is the continuous delivery of these factors which avoids regular dosing. Furthermore, other useful or helpful proteins can be delivered additionally, for example growth factors and/or drugs. Drugs that are useful in this regard are for example anti-inflammatory agents, anti-viral agents and/or antibiotics that prevent or decrease inflammation and/or infection that easily occur on open wounds, particularly on chronic wounds. Furthermore, anti-scar agents can also be useful. Thereby the growth of the tissue is improved and at the same time the quality of the newly built tissue is also enhanced.

Thus, in one embodiment as photosynthetic cells used for the photosynthetic scaffold of the present invention a mixture of *Chlamydomonas* cells is provided with wild-type cells and genetically engineered cells that encode factors, like growth and pro-angiogenic factors, and/or agents like antibacterial or antiviral agents. This embodiment is particularly useful if large wounds on the surface are treated which are prone to infections by bacteria and/or viruses. Furthermore, *Chlamydomonas* cells can be used alone or in combination with other genetically engineered *Chlamydomonas* cells which code for at least one drug having alleviating, mitigating or restoring activity. A combination of cells encoding different agents or the use of cells encoding more than one factor or agent can be used as necessary.

The photosynthetic scaffold of the present invention is not only useful for fresh wounds, for example burns or abrasions, but also for chronic wounds, for example ulceration or decubitus which occurs particularly with elder people.

As outlined above growth factors can be included in the photosynthetic scaffold of the present invention, in particular in the different types of scaffold as outlined above. Growth factors for the growth of tissue are necessary at different times. By regulating the delivery of the growth factors, for example by providing microencapsulated growth factors that deliver at a predetermined time, this problem can be overcome. If growth factors have to be dosed from outside it is difficult to apply them in the appropriate dosage and time period. According to the present invention the growth factors can also be supplied by growing genetically engineered photosynthetic cells and, therefore, the appropriate dosage can be adapted by dosing the engineered cells accordingly. Moreover, the genetically engineered photosynthetic cells can provide growth and angiogenesis factors locally and trigger growth at sites where it is necessary. The local administration avoids side effects that occur with systemic administration of growth factors and angiogenesis factors. As the genetically engineered photosynthetic cells produce the factors continuously and can provide them in the dosage necessary, the dosage can be as low as possible and severe side effects can be avoided.

A further advantage of using photosynthetic cells as oxygen carrier is the property that they can be killed easily just by deprivation of light and/or by using a herbicide which is detrimental to algae cells but not to mammalian cells. Thus, the growth of the algae can be adapted according to the needs of the tissue and can be destroyed immediately if they are no longer necessary or useful.

The present invention is explained in more detail in the following example and the figures. The example and the figures describe preferred embodiments and are not intended to restrict the scope of the invention.

FIG. 1 shows schematically how scaffolds of the present invention work. A standard scaffold is seeded with photosynthetically active cells (1) that when exposed to light release oxygen (2).

Figure 2:
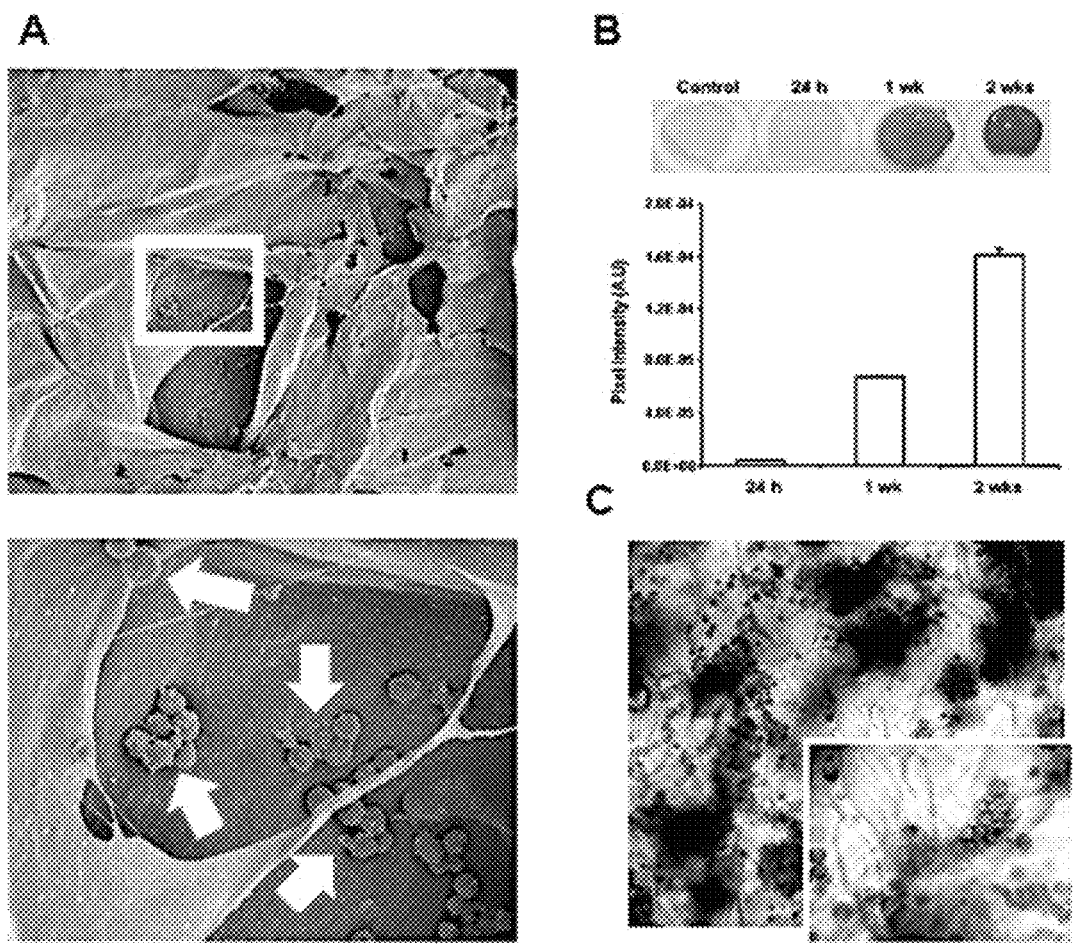

FIG. 2 shows micrographs of *Chlamydomonas* cells seeded on a scaffold of the present invention. A; SEM shows the presence of photosynthetic cells in the inner cavities of the scaffold. Lower picture represents a magnified area and white arrows shows some algae. B; the proliferation of *Chlamydomonas* in dermal scaffolds was determined by quantifying increase in the pixel intensity along the time. C. Shows a microscopic view of algae 7 days after seeding. Results show high biocompatibility and proliferation of *Chlamydomonas* in dermal scaffolds.

Figure 3:
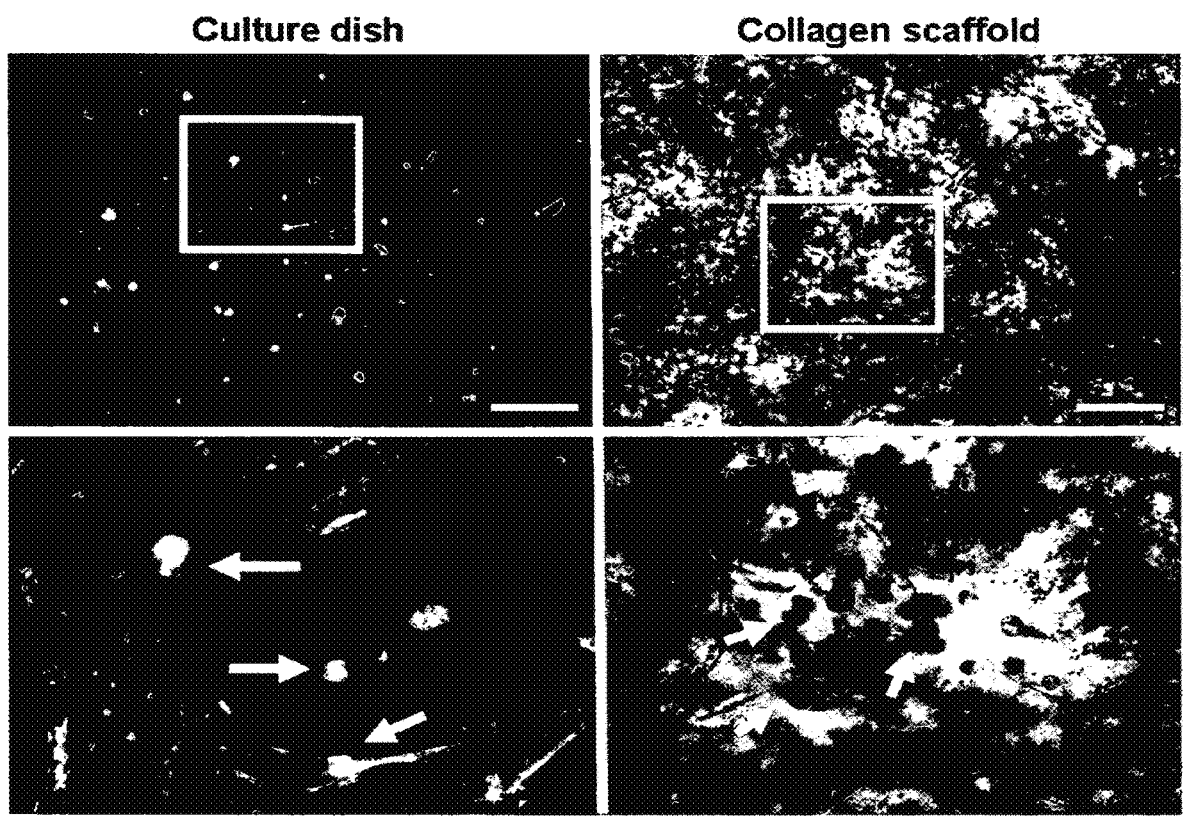

FIG. 3 shows micrographs of cell co-culture. *Chlamydomonas* cells and fibroblasts were co-cultured in dishes and on a scaffold for dermal regeneration. The micrographs on the left show the distribution of *Chlamydomonas* and fibroblasts in a culture dish. Both types of cells can be distinguished by their color and morphology-*Chlamydomonas* (white and round) are indicated with arrows. The micrographs on the right show that in the presence of *Chlamydomonas* the fibroblasts in a collagen scaffold remain metabolically active after 1 week in co-culture. Metabolic activity can be observed as dark dots in the cells (MTT assay). Scale bar represent 100 .mu.m.

Figure 4:
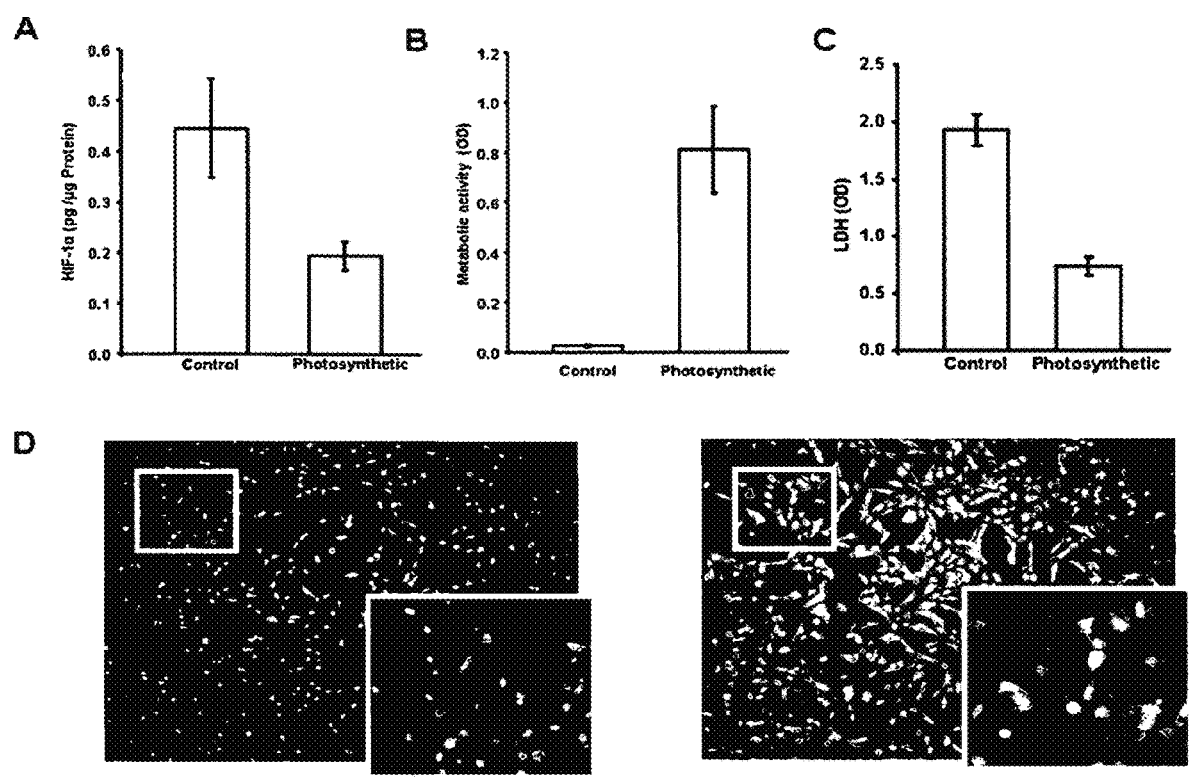

FIG. 4 shows a block diagram wherein hypoxia and metabolic activity have been plotted for fibroblasts growing on photosynthetic scaffolds (comprising photosynthetic cells, according to the present invention) and on standard scaffolds (without photosynthetic cells, for control). The mouse fibroblasts were incubated under hypoxic conditions (1% O.sub.2). As can be seen in the diagram, after 24 hours fibroblasts seeded in control scaffolds express higher levels of the hypoxic marker HIF-1.alpha. (A), metabolic activity was substantially increased in photosynthetic scaffolds (B) and cell death was reduced (C). Moreover, massive cell death induced by hypoxia was inhibited under co-culture conditions (D). In this assay live and dead cells in control (left) and photosynthetic conditions (right) are represented in green and red respectively, which can not be observed in gray scale.

Figure 5:
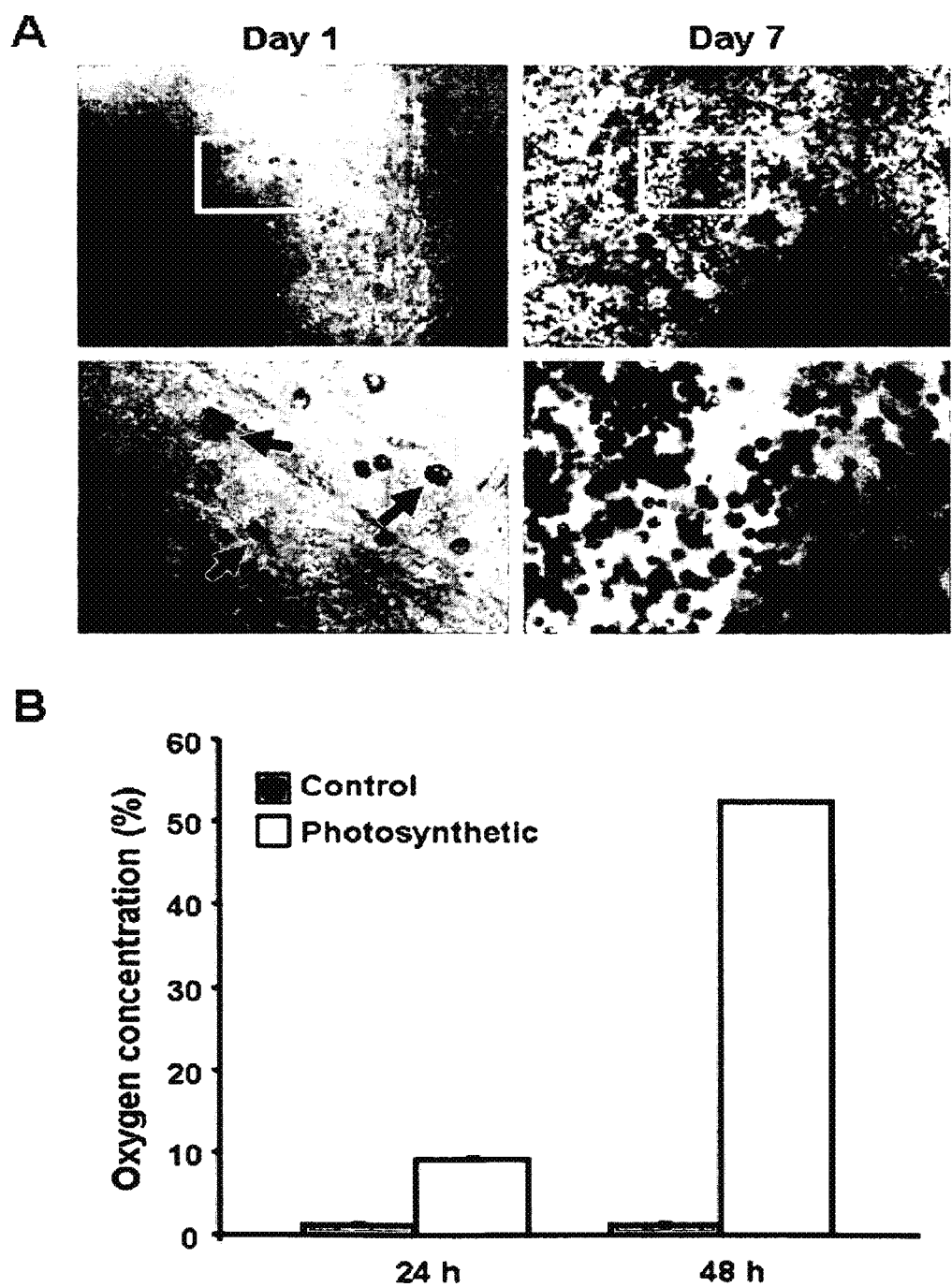

FIG. 5 shows the behavior of *Chlamydomonas* in a bio film. Algae were mixed with fibrin and sprayed over a plastic surface. A: High proliferation of algae (black arrows) was observed 1 week after seeding. B: After hypoxic incubation (1% O.sub.2), the presence of light induce increase of oxygen from 1% up to 50% after 48 hours.

Figure 6:
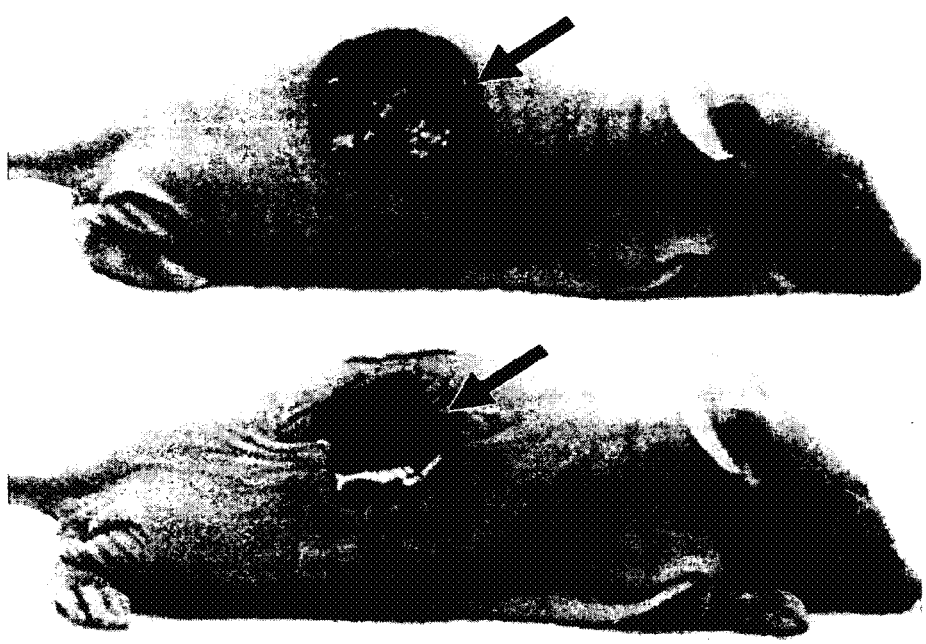

FIG. 6 shows images of a full skin defect model. Animals are anesthetized and areas of skin—1.5 cm diameter—are surgically removed and replaced by scaffolds of the present invention containing photosynthetic cells. Scale bar represent 1 cm.

Figure 7:
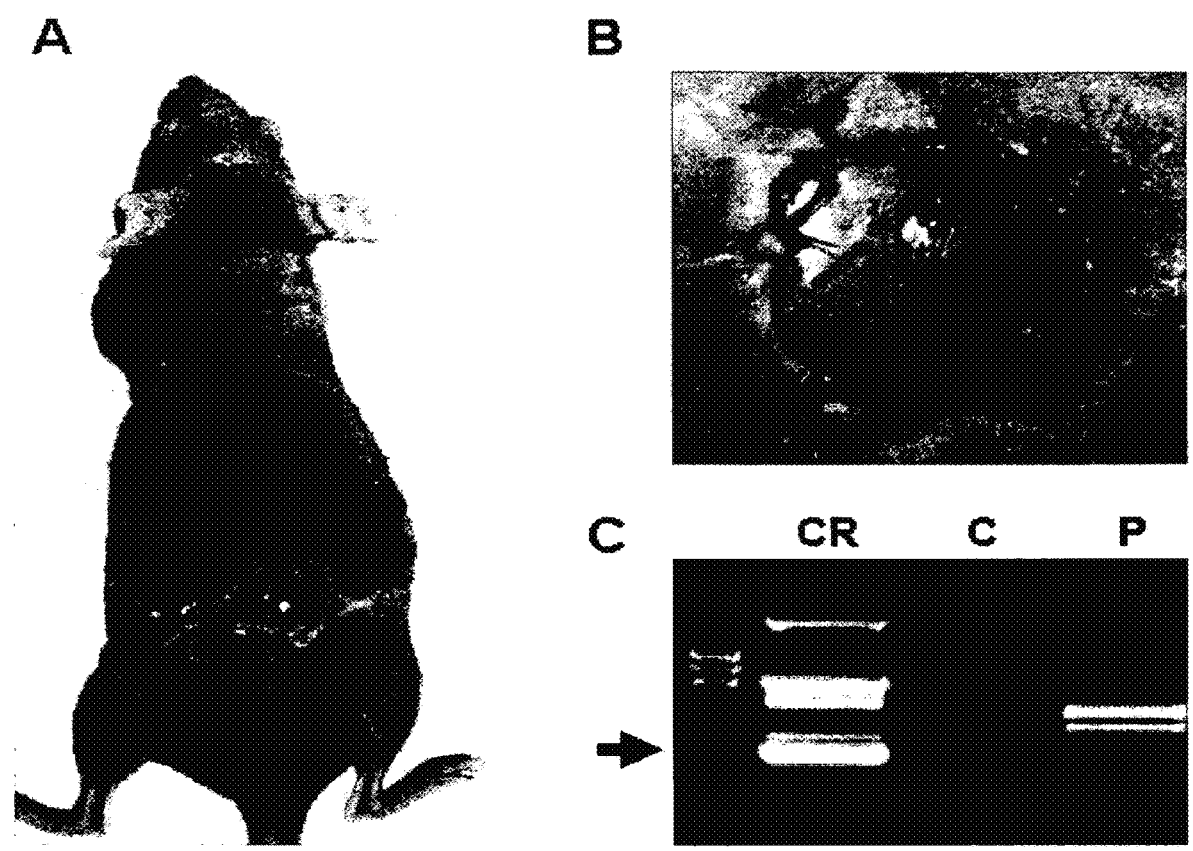

FIG. 7 shows an image of an in vivo transplantation. After 1 week of transplantation animals were sacrificed and the skin graft was removed. It was found that the dermis of the animal presents a light-green color due to the presence of chlorophyll in the tissue in regeneration (panels A-B). Moreover, PCR analysis showed that algae can survive after transplantation (panel C). A specific band for algae was found to be expressed in photosynthetic scaffold (labeled "P" in panel C) but not in controls (labeled "C" in panel C). Here *Chlamydomonas* were used as positive control (labeled "CR" in panel C).

EXAMPLE 1

Experiments in vitro and in vivo have been performed to show the favorable properties of the photosynthetic scaffolds of the present invention.

In a first test it was evaluated if algae of the species *Chlamydomonas reinhardtii* (CR) are able to grow in a collagen scaffold. CR were cultured in vitro in a scaffold that is known for tissue engineering. As shown in FIG. 2, biocompatibility of the CR in the scaffold results in a high proliferation capacity of the algae. After showing that CR can be cultivated in the scaffold, they were grown with mouse fibroblast (NIH 3T3 cells). FIG. 3 shows the interaction and distribution of both cells in normal culture dishes (FIG. 3 left) and in the collagen scaffold (FIG. 3 right). Viability of fibroblast was evaluated by metabolic assay (MTT) and viability of CR was confirmed by direct visualization of the cells by light microscopy (mobility).

In order to determine whether the "photosynthetic scaffold" can support the metabolic requirements of fibroblasts, CR and NIH 3T3 were co-cultured under hypoxic condition (1% O.sub.2) in the presence of a light source. Oxygen was constantly monitored by a commercially available system (PreSens, Regensburg, Germany). Results show that the photosynthetic scaffold allows to significantly reduce the hypoxic marker HIF-1.alpha. (FIG. 4A). Moreover, under such conditions metabolic activity was drastically increased (FIG. 4B) and cell death was decreased (FIG. 4C). Finally, live/dead studies, performed in cell culture dishes, show that when cells are incubated during 4 days under hypoxic conditions almost all cells are dead (FIG. 4D; left). In contrast to that the presence of the algae fully avoids such effect (FIG. 4D; right).

Next, similar experiments were performed in a bio-film containing CR. As shown in FIG. 5, CR are able to proliferate in fibrin (FIG. 5A), releasing significant amounts of oxygen (FIG. 5B).

The feasibility of this approach was evaluated in vivo. For that, a bilateral full skin defect was created in the back of 6 nude mice and the skin was replaced by a scaffold containing 5.times.10.sup.6 CR (FIG. 6). 1 week after of transplantation, the scaffolds were removed and integration and viability of the algae in the new tissue was analyzed. Results showed that animals can survive after transplantation, presenting a light-green color of the dermis in regeneration (FIG. 7A). Moreover, presence of RNA derived from the algae showed that algae were metabolically active 1 week after implantation (FIG. 7B).

Moreover, long term in vivo experiments have been carried out. The results show that animals can survive for at least 2 months in the presence of "photosynthetic scaffolds" containing algae.

What is claimed is:

1. A method for treating injured tissue, comprising applying a structure or carrier matrix seeded with photosynthetically active cells to the injured tissue such that the photosynthetically active cells directly contact the injured tissue, wherein the photosynthetically active cells deliver oxygen to the injured tissue.

2. The method of claim 1, wherein the photosynthetically active cells are from the genus *Chlamydomonas*.

3. The method of claim 2, wherein the *Chlamydomonas* is *Chlamydomonas reinhardtii*.

4. The method of claim 1, wherein the photosynthetically active cells are encapsulated with a permeable immunologically inert material.

5. The method of claim 4, wherein the permeable immunologically inert material is a natural or synthetic polymer.

6. The method of claim 5, wherein the natural or synthetic polymer is a hydrogel or alginate.

7. The method of claim 1, wherein at least some of the photosynthetically active cells have been genetically engineered to contain nucleic acids encoding for at least one bioactive molecule.

8. The method of claim 1, wherein the injured tissue comprises damage of at least one of skin, nerve, bone, cartilage and blood tissue.

9. The method of claim 1, wherein at least some of the photosynthetically active cells are genetically engineered cells containing nucleic acids encoding for at least one pro-angiogenic factor.

10. The method of claim 1, wherein the structure or carrier matrix comprises a biofilm.

11. The method of claim 1, wherein applying the structure or carrier matrix seeded with photosynthetic cells hinders hypoxia and increases tissue regeneration.

12. The method of claim 1, wherein the structure or carrier matrix comprises nutrients for growth of the photosynthetically active cells.

13. The method of claim 1, wherein the structure or carrier matrix comprises a wound dressing.

14. The method of claim 1, wherein the structure or carrier matrix comprises a surgical suture.

15. The method of claim 1, wherein the structure or carrier matrix is biocompatible and biodegradable.

16. The method of claim 1, wherein at least some of the photosynthetically active cells are genetically modified cells.

* * * * *